(12) United States Patent
Kumagai

(10) Patent No.: US 11,112,334 B2
(45) Date of Patent: Sep. 7, 2021

(54) IN-VEHICLE EXHAUST GAS ANALYSIS SYSTEM, INSPECTION SYSTEM FOR IN-VEHICLE EXHAUST GAS ANALYSIS SYSTEM, INSPECTION METHOD FOR IN-VEHICLE EXHAUST GAS ANALYSIS SYSTEM, AND INSPECTION PROGRAM

(71) Applicant: HORIBA, Ltd., Kyoto (JP)

(72) Inventor: Tatsuki Kumagai, Kyoto (JP)

(73) Assignee: HORIBA, LTD., Kyoto (JP)

( * ) Notice: Subject to any disclaimer, the term of this patent is extended or adjusted under 35 U.S.C. 154(b) by 465 days.

(21) Appl. No.: 15/690,036

(22) Filed: Aug. 29, 2017

(65) Prior Publication Data

US 2018/0164184 A1 Jun. 14, 2018

(30) Foreign Application Priority Data

Dec. 14, 2016 (JP) .............................. JP2016-242314

(51) Int. Cl.
*F01N 13/00* (2010.01)
*F01N 13/08* (2010.01)
(Continued)

(52) U.S. Cl.
CPC ........... *G01M 15/102* (2013.01); *F01N 11/00* (2013.01); *F01N 13/008* (2013.01); *F01N 13/08* (2013.01);
(Continued)

(58) Field of Classification Search
CPC ...... F01N 11/00; F01N 13/08; F01N 2560/02; F01N 2560/022; F01N 2560/07;
(Continued)

(56) References Cited

U.S. PATENT DOCUMENTS 4,260,886 A * 4/1981 Grilletto ................. H01J 49/26
250/252.1
5,756,360 A * 5/1998 Harvey ................ G01N 1/2252
422/83
(Continued)

FOREIGN PATENT DOCUMENTS

CN 1588087 A 3/2005
CN 2715156 Y 8/2005
(Continued)

OTHER PUBLICATIONS

EESR dated Mar. 22, 2018 issued for European Patent Application No. 17 189 813.3.
(Continued)

*Primary Examiner* — Jeffrey P Aiello
(74) *Attorney, Agent, or Firm* — Brooks Kushman P.C.

(57) ABSTRACT

An in-vehicle exhaust gas analysis system, which is provided with a flowmeter, and an exhaust gas analyzer to analyze a concentration of a measurement target component contained in exhaust gas, includes a standard gas supply mechanism to supply a standard gas containing a predetermined component to the flowmeter and the exhaust gas analyzer. The system is configured to include a detected mass calculation section to calculate a detected mass of a predetermined component by using a flow rate obtained by the flowmeter and a concentration of the predetermined component obtained by the exhaust gas analyzer, a supply mass acquisition section to acquire a supply mass of the predetermined component supplied from the standard gas supply mechanism to the flowmeter and the exhaust gas analyzer, and a mass comparison section to compare a detected mass calculated by the mass calculation section and a supply mass acquired by the supply mass acquisition section.

12 Claims, 4 Drawing Sheets

(51) Int. Cl.

| | | |
|---|---|---|
| *G01M 15/10* | (2006.01) | |
| *G01N 33/00* | (2006.01) | |
| *G01F 1/46* | (2006.01) | |
| *F01N 11/00* | (2006.01) | |
| *G01N 1/22* | (2006.01) | |

(52) U.S. Cl.
CPC ............ *G01F 1/46* (2013.01); *G01N 33/007* (2013.01); *F01N 2560/02* (2013.01); *F01N 2560/022* (2013.01); *F01N 2560/07* (2013.01); *F01N 2560/08* (2013.01); *G01N 1/2252* (2013.01); *G01N 33/004* (2013.01); *G01N 33/0037* (2013.01); *G01N 2033/0072* (2013.01); *Y02A 50/20* (2018.01); *Y02T 10/40* (2013.01)

(58) Field of Classification Search
CPC ............ G01M 15/102; G01N 1/2252; G01N 2033/0072; G01N 2033/007; Y02A 50/245; Y02T 10/47
USPC ....... 60/276; 73/1.34, 23.31; 702/23, 24, 30, 702/50, 108
See application file for complete search history.

(56) References Cited

U.S. PATENT DOCUMENTS

| | | | | |
|---|---|---|---|---|
| 6,200,819 | B1* | 3/2001 | Harvey | G01N 1/2252 422/83 |
| 6,439,040 | B1 | 8/2002 | Garms et al. | |
| 7,610,142 | B1 | 10/2009 | Hoard et al. | |
| 2001/0003915 | A1* | 6/2001 | Inoue | G01N 1/2252 73/23.2 |
| 2003/0029221 | A1* | 2/2003 | Juneau | G01N 15/0618 73/1.02 |
| 2004/0007056 | A1* | 1/2004 | Webb | F23D 11/107 73/114.77 |
| 2004/0064243 | A1* | 4/2004 | Nakamura | F01N 13/008 701/114 |
| 2004/0149595 | A1* | 8/2004 | Moore | F01N 3/28 205/784.5 |
| 2005/0099001 | A1* | 5/2005 | Cassel | F01N 13/1805 285/23 |
| 2010/0242460 | A1* | 9/2010 | Sponsky | F01N 13/20 60/320 |
| 2017/0114998 | A1* | 4/2017 | Mueller | F02B 23/0651 |

FOREIGN PATENT DOCUMENTS

| | | |
|---|---|---|
| CN | 1888857 A | 1/2007 |
| CN | 201000394 Y | 1/2008 |
| CN | 102445518 A | 5/2012 |
| CN | 102749378 A | 10/2012 |
| JP | 09-318572 A | 12/1997 |
| JP | 2001-165827 A | 6/2001 |
| JP | 2001-523317 A | 11/2001 |
| JP | 2002098618 A | 4/2002 |
| JP | 2004-117261 A | 4/2004 |
| JP | 2010-276473 A | 12/2010 |
| JP | 2015-222251 A | 12/2015 |

OTHER PUBLICATIONS

Nobutaka Kihara, "The OBS-1000 Series On-vehicle Engine Exhaust Gas Measuring Systems, Readout", Japan, Horiba, Ltd., 2005, No. 30, pp. 56 to 61, https://www.horiba.com/jp/publications/readout/article/obs-1000 to 1096/F.

Office Action dated Dec. 19, 2019 issued for Japanese Patent Application No. 2016-242314, 8 pgs.

Nobutaka Kihara, "The OBS-1000 Series On-board Engine Emission Measurement System", Readout English Edition, No. 9, pp. 64-71, Dec. 31, 2005.

Office Action dated Jul. 2, 2021 issued in CN patent application No. 201710761524.6, 36 pgs.

* cited by examiner

IN-VEHICLE EXHAUST GAS ANALYSIS SYSTEM, INSPECTION SYSTEM FOR IN-VEHICLE EXHAUST GAS ANALYSIS SYSTEM, INSPECTION METHOD FOR IN-VEHICLE EXHAUST GAS ANALYSIS SYSTEM, AND INSPECTION PROGRAM

CROSS-REFERENCE TO RELATED APPLICATION

This application claims priority to JP Application No. 2016-242314, filed Dec. 14, 2016, the disclosure of which is incorporated in its entirety by reference herein.

BACKGROUND OF THE INVENTION

Field of the Invention

The present invention relates to an in-vehicle exhaust gas analysis system, an inspection system for an in-vehicle exhaust gas analysis system, an inspection method for an in-vehicle exhaust gas analysis system, and an inspection program.

Background Art

A vehicle test includes a road travel (driving) test to measure exhaust gas discharged from a tailpipe of a vehicle during road traveling.

In the road driving test, as illustrated in Patent Document 1, various kinds of exhaust gas analyzers are mounted in the vehicle, and the exhaust gas discharged from the tailpipe is sampled to analyze each component contained in the exhaust gas. A flowmeter for measuring a flow rate of the exhaust gas is disposed on the tailpipe, and calculates a discharge mass of each component from an exhaust gas flow rate obtained by the flowmeter, and a concentration of each component obtained by the exhaust gas analyzer.

A method of inspecting accuracy of the in-vehicle exhaust gas analysis system is performed using a constant volume sampler (CVS).

Specifically, the vehicle is subjected to a simulated drive on a chassis dynamometer in a predetermined travel pattern (driving cycle), and an emission mass of a measurement target component is calculated from, for example, a concentration of the measurement target component in a diluted exhaust gas collected into a collecting bag by using the CVS, a flow rate of the CVS, and sampling time. The discharge mass obtained by the collecting bag serves as a reference. Similarly, a vehicle having an in-vehicle exhaust gas analysis system mounted therein is subjected to simulated driving on the chassis dynamometer in the predetermined driving cycle. An emission mass of a measurement target component is calculated from, for example, a concentration of the measurement target component obtained during the simulated drive, a sampling flow rate, and sampling time. Then, the accuracy of the in-vehicle exhaust gas analysis system is inspected by comparing the emission mass obtained by the collecting bag and the emission mass obtained by the in-vehicle exhaust gas analysis system.

However, the inspection of the in-vehicle exhaust gas analysis system necessitates the measurement of the emission mass by collecting the diluted exhaust gas into the collecting bag with the use of the CVS. Additionally, not only the measurement of the emission mass by using the collecting bag, but also the measurement of the emission mass by using the in-vehicle exhaust gas analysis system necessitates the simulated driving of the vehicle by operating the chassis dynamometer. Hence, the conventional inspection method has the problem that the inspection time becomes longer. Besides this, the conventional inspection method also necessitates a preparation work for operating the chassis dynamometer and a work for carrying the in-vehicle exhaust gas analysis system that has been mounted in an actual vehicle into a test room in which the CVS is disposed. Hence, there arises the problem that an inspection operation. becomes complicated.

PRIOR ART DOCUMENT

Patent Document

Patent Document 1: Japanese Unexamined Patent Publication No. 2004-117261

SUMMARY OF THE INVENTION

Problems to be Solved by the Invention

Accordingly, the present invention has been made to solve the above problems, and has for its main object to simply inspect the entirety of an in-vehicle exhaust gas analysis system combining a flowmeter and an exhaust gas analyzer.

Means of Solving the Problems

An in-vehicle exhaust gas analysis system according to the present invention is one which includes a flowmeter to measure a flow rate of exhaust gas discharged from a vehicle, and an exhaust gas analyzer to analyze a concentration of a measurement target component contained in the exhaust gas. The system includes a standard gas supply mechanism, a detected mass calculation section, a supply mass acquisition section, and a mass comparison section. The standard gas supply mechanism supplies a standard gas containing a predetermined component to the flowmeter and the exhaust gas analyzer. The detected mass calculation section calculates a detected mass of the predetermined component by using a flow rate obtained by the flowmeter and a concentration of the predetermined component obtained by the exhaust gas analyzer. The supply mass acquisition section acquires a supply mass of the predetermined component supplied from a standard gas supply mechanism to the flowmeter and the exhaust gas analyzer. The mass comparison section compares the detected mass calculated by the mass calculation section and the supply mass acquired by the supply mass acquisition section.

Alternatively, an in-vehicle exhaust gas analysis system according to the present invention is one which includes a flowmeter to measure a flow rate of exhaust gas discharged from a vehicle, and an exhaust gas analyzer to analyze a concentration of a measurement target component contained in the exhaust gas. The analysis system is configured to be supplied with a standard gas containing a predetermined component. The system includes a detected mass calculation section, a supply mass acquisition section, and a mass comparison section. The detected mass calculation section calculates a detected mass of the predetermined component by using a flow rate obtained by the flowmeter and a concentration of the predetermined component obtained by the exhaust gas analyzer. The supply mass acquisition section acquires a supply mass of the predetermined component supplied from a standard gas supply mechanism to the flowmeter and the exhaust gas analyzer. The mass comparison section compares a detected mass calculated by the mass calculation section and a supply mass acquired by the supply mass acquisition section.

An inspection system for an in-vehicle exhaust gas analysis system according to the present invention is the inspection system for the in-vehicle exhaust gas analysis system including a flowmeter to measure a flow rate of exhaust gas discharged from a vehicle, and an exhaust gas analyzer to analyze a concentration of a measurement target component contained in the exhaust gas. The inspection system includes a standard gas supply mechanism, a detected mass calculation section, a supply mass acquisition section, and a mass comparison section. The standard gas supply mechanism supplies a standard gas containing a predetermined component to the in-vehicle exhaust gas analysis system. The detected mass calculation section calculates a detected mass of the predetermined component by using a flow rate obtained by the flowmeter and a concentration of the predetermined component obtained by the exhaust gas analyzer. The supply mass acquisition section acquires a supply mass of the predetermined component supplied from the standard gas supply mechanism to the in-vehicle exhaust gas analysis system. The mass comparison section compares the detected mass calculated by the mass calculation section and the supply mass acquired by the supply mass acquisition section.

Yet alternatively, an in-vehicle exhaust gas analysis system according to the present invention is one which includes a flowmeter to measure a flow rate of exhaust gas discharged from a vehicle, and an exhaust gas analyzer to analyze a concentration of a measurement target component contained in the exhaust gas. The analysis system includes a standard gas supply mechanism to supply a standard gas containing a predetermined component to the flowmeter and the exhaust gas analyzer. The analysis system also includes a detected mass calculation section, a supply mass acquisition section, and a mass comparison section. The detected mass calculation section calculates a detected mass of the predetermined component by using a flow rate obtained by the flowmeter and a concentration of the predetermined component obtained by the exhaust gas analyzer. The supply mass acquisition section acquires a supply mass of the predetermined component supplied from the standard gas supply mechanism to the in-vehicle exhaust gas analysis system. The mass comparison section compares the detected mass calculated by the mass calculation section and the supply mass acquired by the supply mass acquisition section.

An inspection method for an in-vehicle exhaust gas analysis system according to the present invention is a method of inspecting the in-vehicle exhaust gas analysis system including a flowmeter to measure a flow rate of exhaust gas discharged from a vehicle, and an exhaust gas analyzer to analyze a concentration of a measurement target component by supplying thereto a standard gas containing a predetermined component. The inspection method includes: a detected mass calculation step of calculating a detected mass of the predetermined component supplied to the in-vehicle exhaust gas analysis system by using the flow rate obtained by the flowmeter and the concentration of the predetermined component obtained by the exhaust gas analyzer; a supply mass acquisition step of acquiring a supply mass of the predetermined component supplied to the in-vehicle exhaust gas analysis system; and a mass comparison step of comparing the detected mass calculated by the mass calculation step and the supply mass obtained by the supply mass acquisition step.

An inspection program used for an in-vehicle exhaust gas analysis system according to the present invention is one which is used for the in-vehicle exhaust gas analysis system which includes a flowmeter to measure a flow rate of exhaust gas discharged from a vehicle, and an exhaust gas analyzer to analyze a concentration of a measurement target component contained in the exhaust gas, and which is configured to be supplied with a standard gas containing a predetermined component. The inspection program causes a computer to have functions as: a detected mass calculation section to calculate a detected mass of the predetermined component supplied to the in-vehicle exhaust gas analysis system by using the flow rate obtained by the flowmeter and the concentration of the predetermined component obtained by the exhaust gas analyzer; a supply mass acquisition section to acquire a supply mass of the predetermined component supplied from a standard gas supply mechanism to the in-vehicle exhaust gas analysis system; and a mass comparison section to compare a detected mass calculated by the mass calculation section and a supply mass obtained by the supply mass acquisition section.

With the foregoing configurations, the standard gas containing the predetermined component is supplied to the in-vehicle exhaust gas analysis system, and the comparison is made between the detected mass calculated from the flow rate obtained by the flowmeter and the concentration of the predetermined component obtained by the exhaust gas analyzer, and the supply mass of the predetermined component supplied to the in-vehicle exhaust gas analysis system. Therefore, the in-vehicle exhaust gas analysis system is simply inspectable without the use of the CVS that has been used conventionally. Because there is no need to use the CVS, it is possible to eliminate the need for the preparation work for operating the chassis dynamometer and the work for carrying the in-vehicle exhaust gas analysis system that has been mounted in the actual vehicle into the test room in which the CVS is disposed.

The predetermined component of the standard gas is preferably a component contained in the exhaust gas in order to accurately inspect the in-vehicle exhaust gas analysis system. In other words, the standard gas supply mechanism supplies a standard gas containing a component contained in exhaust gas to the in-vehicle exhaust gas analysis system. Because the exhaust gas analyzer is configured to ensure high accuracy with respect to a component to be measured, the use of the standard gas containing the component contained in the exhaust gas makes it possible to enhance inspection accuracy of the exhaust gas analyzer.

The flowmeter preferably includes a mounting tube externally attached to an exhaust pipe of the vehicle. The standard gas supply mechanism preferably includes a standard gas supply tube to supply the standard gas to the mounting tube. The standard gas supply tube preferably has a diameter approximately equal to that of the mounting tube.

With this configuration, the flow rate of the standard gas flowing through the interior of the mounting tube and the flow rate of the standard gas flowing through the standard gas supply tube can be made approximately equal, thereby making it easier to maintain the flow rate of the standard gas flowing through the interior of the mounting tube within a predetermined range.

In order to ensure that the inspection is performed by variously changing the concentration and flow rate of a predetermined component supplied to the in-vehicle exhaust gas analysis system, the standard gas supply mechanism preferably includes a flow rate regulation section to regulate a flow rate of the standard gas supplied to the in-vehicle exhaust gas analysis system.

In order to make it possible to variously change the concentration of a predetermined component supplied to the flowmeter and the exhaust gas analyzer, the in-vehicle exhaust gas analysis system is preferably configured to supply a mixed gas comprised of the standard gas and atmospheric air to the flowmeter and the exhaust gas analyzer, and it is preferable to further include a flow rate regulating mechanism to regulate the flow rate of the mixed gas.

In order to ensure that the inspect is performed at each of flow rates within a measurement range of the flowmeter of the in-vehicle exhaust gas analysis system, the flow rate regulation section is preferably one which is configured to stepwise or continuously change the flow rate of the mixed gas within the measurement range of the flowmeter.

As other embodiment for ensuring that the inspection is performable by variously changing the concentration and flow rate of the predetermined component supplied to the in-vehicle exhaust gas analysis system, the standard gas supply mechanism preferably further includes a supply-side flow rate regulation section to regulate the flow rate of the standard gas supplied to the flowmeter and the exhaust gas analyzer.

In order to accurately inspect the in-vehicle exhaust gas analysis system, it is preferable to further include a background correction section to perform a background correction of the detected mass used in the mass comparison section.

Effects of the Invention

With the present invention so configured, the standard gas containing the predetermined component is supplied to the in-vehicle exhaust gas analysis system, and the comparison is made between the detected mass calculated from the flow rate of the standard gas obtained by the flowmeter and the concentration of the predetermined component obtained by the exhaust gas analyzer, and the supply mass of the predetermined component supplied to the in-vehicle exhaust gas analysis system. Therefore, the in-vehicle exhaust gas analysis system is simply inspectable without the use of the CVS that has been used conventionally.

MODE FOR CARRYING OUT THE INVENTION

An embodiment of an inspection system for an in-vehicle exhaust gas analysis system according to the present invention is described below with reference to the drawings.
<In-Vehicle Exhaust Gas Analysis System>
Firstly, the in-vehicle exhaust gas analysis system 10 is described below.

Figure 1:
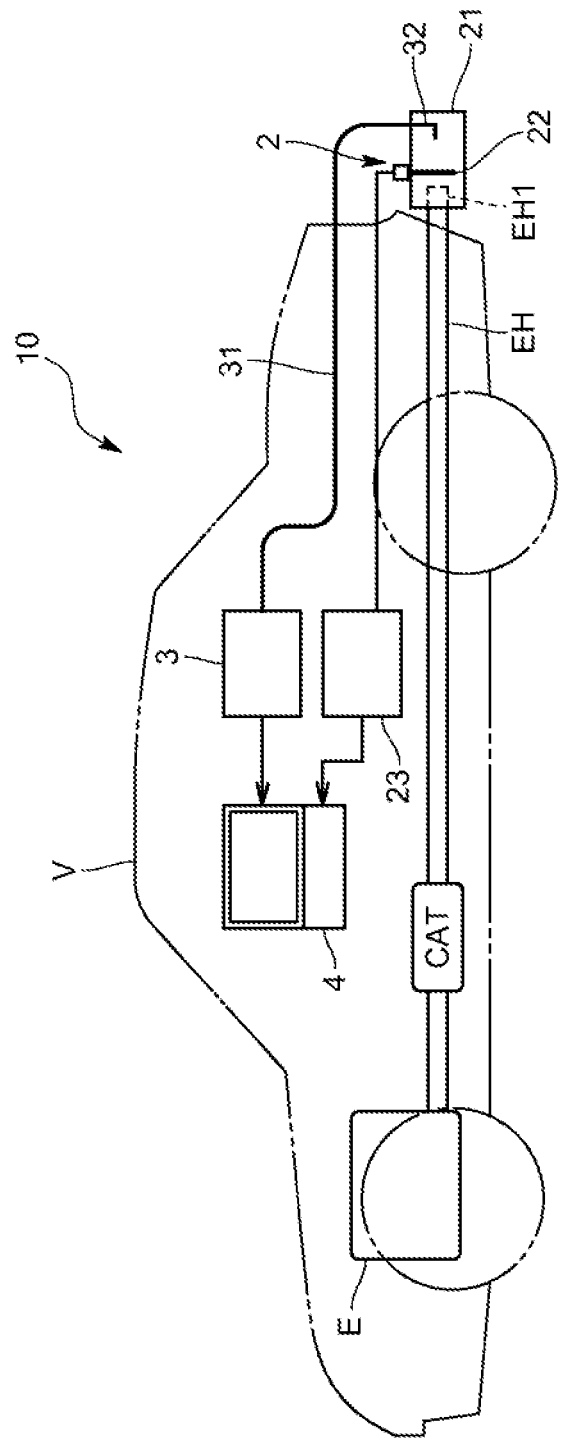
FIG. 1 is a schematic diagram that shows a configuration of an in-vehicle exhaust gas analysis system according to the present embodiment.

As shown in FIG. 1, the in-vehicle exhaust gas analysis system 10 is one which is mounted in a vehicle V and configured to analyze exhaust gas discharged from an internal combustion engine E of the vehicle when the vehicle V drives on a road, in real time during the driving on the road. The in-vehicle exhaust gas analysis system 10 employs a direct sampling method of directly measuring a concentration of collected exhaust gas without diluting the collected exhaust gas.

The in-vehicle exhaust gas analysis system 10 includes a flowmeter 2 to measure a flow rate of exhaust gas discharged from the vehicle V, and a gas analyzer 3 to analyze a concentration of a measurement target component contained in the exhaust gas.

The flowmeter 2 is attached to an opening end portion EH1 of an exhaust pipe EH being coupled to the internal combustion engine E, and is configured to measure a flow rate of the exhaust gas discharged from the exhaust pipe EH. Specifically, the flowmeter 2 is configured to detect a differential pressure of exhaust gas flowing through a flow channel, and calculate the flow rate of the exhaust gas from the differential pressure. The flowmeter 2 includes a mounting tube externally attached to the opening end portion EH1 of the exhaust pipe EH, a differential pressure detection section 22 to detect a differential pressure of exhaust gas flowing through the mounting tube 21, and a flow rate calculation section 23 to calculate a flow rate of exhaust gas by using the differential pressure obtained by the differential pressure detection section 22.

The mounting tube 21 has a straight pipe-shaped one attached to the opening end portion EH1 of the exhaust pipe EH, and is a circular tube whose cross section is a circular form in the present embodiment. An opening at one end of the mounting tube 21 is attached to the opening end portion EH1 of the exhaust pipe EH, and an opening at the other end is opened. The opening at the other end permits discharge of exhaust gas therethrough to the exterior.

A differential pressure detection section 22 is intended to detect a differential pressure between a total pressure and a static pressure of exhaust gas. The differential pressure detection section 22 includes a pitot tube having a total pressure hole for detecting a total pressure and a static pressure hole for detecting a static pressure, and a differential pressure sensor, such as a differential pressure transmitter, which detects, through the pitot tube, a differential pressure ΔP between the total pressure and the static pressure of the exhaust gas.

The flow rate calculation section 23 calculates a volumetric flow rate $Q_{exh}(t)$ [m$^3$/min] of exhaust gas in a standard state according to the following equation and from the differential pressure ΔP obtainable from the differential pressure sensor of the differential pressure detection section 22, an exhaust gas temperature $T_{exh}(t)$ [K] obtainable from an exhaust gas thermometer (not shown) disposed at the mounting tube 21, and an exhaust gas pressure $P_{exh}(t)$ [kPa] obtainable from an absolute manometer (not shown) disposed at the mounting tube 21.

$$Q_{exh}(t) = k \times \sqrt{\frac{P_{exh}(t)}{P_0} \times \frac{T_0}{T_{exh}(t)} \times \frac{\Delta P}{\rho_{exh}}} \qquad \text{[Equation 1]}$$

Here, k is a proportionality coefficient, $P_0$ is a standard pressure (101.3 [kPa]), $T_0$ is a standard temperature (293.15 [K]), and $\rho_{exh}$ is an exhaust gas density [g/min$^3$] in the standard state.

The proportionality coefficient K, standard pressure $P_0$, standard temperature $T_0$, and exhaust gas density $\rho_{exh}$ are previously input.

The gas analyzer 3 is intended to continuously measure a concentration of a measurement target component contained in exhaust gas (for example, CO, $CO_2$, $CO_0$, $NO_x$, and THC). When the gas analyzer 3 is intended to measure the concentration of CO and $CO_2$, an NDIR detector using non-dispersive infrared absorption method (NDIR method) is usable. When the gas analyzer 3 is intended to measure the concentration of $NO_x$, a CLD detector using chemiluminescence analysis method (CLD method) is usable. When the gas analyzer 3 is intended to measure the concentration of THC, an FID detector using flame ionization analysis method (FID) is usable. The gas analyzer 3 may include any one of these detectors or a plurality of kinds of these detectors. Alternatively, the gas analyzer 3 may be such a detector that uses different analysis methods according to a measurement target component.

A loading tube 31 for loading sampled exhaust gas is coupled to the gas analyzer 3. One end of the loading tube 31 is coupled to the gas analyzer 3, and a sampling section 32 for sampling exhaust gas is disposed at the other end of the loading tube 31. The sampling section 32 is disposed on the mounting tube 21 of the flowmeter 2 described above. The sampling section 32 is composed of a sampling tube through which part of exhaust gas flowing through the mounting tube 21 is collected.

Concentration signals of individual components obtained by the gas analyzer 3 are transmitted to a host arithmetic unit 4 and used for computing an emission mass of each of the components, together with a flowrate signal outputted from the flow rate calculation section 23 of the differential pressure flowmeter 2.

<Inspection System>

An inspection system 100 is described below.

The inspection system 100 is intended to inspect both the flowmeter 2 and the gas analyzer 3 in the in-vehicle exhaust gas analysis system 10. The in-vehicle exhaust gas analysis system to be inspected by the inspection system 100 may be in a state in which at least the mounting tube 21 of the flowmeter 2 is removed from the exhaust pipe EH of the vehicle V, and the gas analyzer 3 is mounted in the vehicle. The present embodiment describes the inspection system 100 in cases where the gas analyzer 3 is the NDIR detector to measure the concentrations of CO and $CO_2$.

Figure 2:
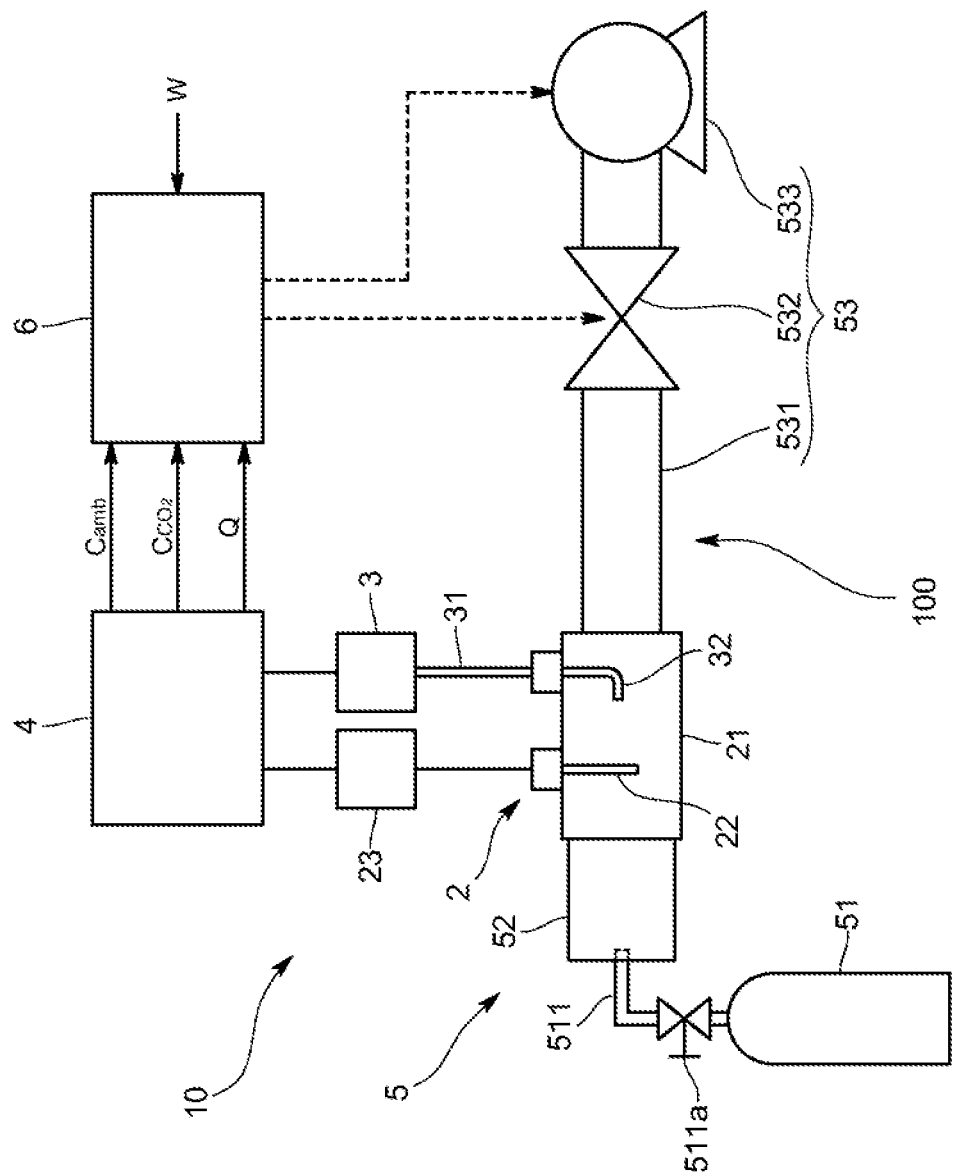
FIG. 2 is a schematic diagram that shows a configuration of an inspection system in the present embodiment.

Specifically, as shown in FIG. 2, the inspection system 100 includes a standard gas supply mechanism 5 to supply a standard gas containing a predetermined component to the in-vehicle exhaust gas analysis system 10, and an information processor 6 to perform information processing for inspecting the accuracy of the in-vehicle exhaust gas analysis system 10.

The standard gas supply mechanism 5 is intended to supply the standard gas having a predetermined flow rate to the in-vehicle exhaust gas analysis system 10. The standard gas supply mechanism 5 includes a standard gas source 51, such as a standard gas cylinder, a standard gas supply tube 52 to supply the standard gas from the standard gas source 51 to the in-vehicle exhaust gas analysis system 10, and a flow rate regulation section 53 to regulate a flow rate of the standard gas supplied to the in-vehicle exhaust gas analysis system 10.

The standard gas source 51 is a $CO_2$ gas cylinder filled with $CO_2$ gas in the present embodiment. An opening/closing valve 511a is disposed at a gas supply port 511 of the $CO_2$ gas cylinder. The opening/closing valve 511a is openable and closable manually or automatically by the information processor 6, or the like.

One end of the standard gas supply tube 52 is coupled to the gas supply port 511 of the $CO_2$ gas cylinder 51, and the other end thereof is coupled to one end opening of the mounting tube 21 of the flowmeter 2. Here, the one end of the standard gas supply tube 52 is coupled to the gas supply port 511 so as to permit inflow of ambient air (atmospheric air) together with the $CO_2$ gas. Specifically, the one end opening of the standard gas supply tube 52 is made larger than the gas supply port 511 of the $CO_2$ gas cylinder 51, thereby permitting the inflow of the atmospheric air from around the gas supply port 511. The standard gas supply tube 52 in the present embodiment is a straight circular tube whose cross section is a circular form, and has approximately the same diameter (approximately the same inner diameter) as the mounting tube 21.

The flow rate regulation section 53 is intended to regulate a flow rate of a mixed gas of the $CO_2$ gas (standard gas) flowing into the mounting tube 21 of the flowmeter 2 and the atmospheric air so as to reach a predetermined value. Specifically, the flow rate regulation section 53 includes a standard gas discharge tube 531 coupled to the other end opening of the mounting tube 21 of the flowmeter 2, and a flow rate regulating valve 532 and a suction pump 533 which are disposed on the standard gas discharge tube 531.

Similarly to the standard gas supply tube 52, the standard gas discharge tube 531 is a straight circular tube whose cross section is a circular form, and can be made into one which has approximately the same diameter as the mounting tube 21.

The flow rate regulating valve 532 is capable of regulating the flow rate of the standard gas flowing through the mounting tube 21 of the flowmeter 2 so as to reach an arbitrary flow rate, and, for example, an electric-operated valve is usable therefor. The standard gas flowing through the mounting tube 21 of the flowmeter 2 can be made constant by regulating a valve opening degree of the flow rate regulating valve 532 and then sucking the standard gas by the suction pump 533. The valve opening degree of the flow rate regulating valve 532 is controlled by the information processor 6. A rotational speed of the suction pump 533 is also controlled by the information processor 6.

Thus, the mounting tube 21 of the flowmeter 2 in the in-vehicle exhaust gas analysis system 10 is coupled to the standard gas supply tube 52 and the standard gas discharge tube 531, and the standard gas flowing through the mounting tube 21 is regulated by the flow rate regulating valve 532. On this occasion, a flow rate is measured by the flowmeter 2 of the in-vehicle exhaust gas analysis system 10, the standard gas is sampled by the sampling section 32, and a $CO_2$ concentration in the standard gas is measured by the gas analyzer 3. Signals respectively indicating these values are transmitted to the information processor 6 described below.

The information processor 6 is intended to inspect the accuracy of the in-vehicle exhaust gas analysis system 10 by using the flow rate of the standard gas obtained by the flowmeter 2, and the $CO_2$ concentration of the standard gas obtained by the gas analyzer 3. The information processor 6 is a so-called computer including, for example, a CPU, memory, and an input/output interface. Alternatively, the information processor 6 may be configured by using the arithmetic unit 4.

Figure 3:
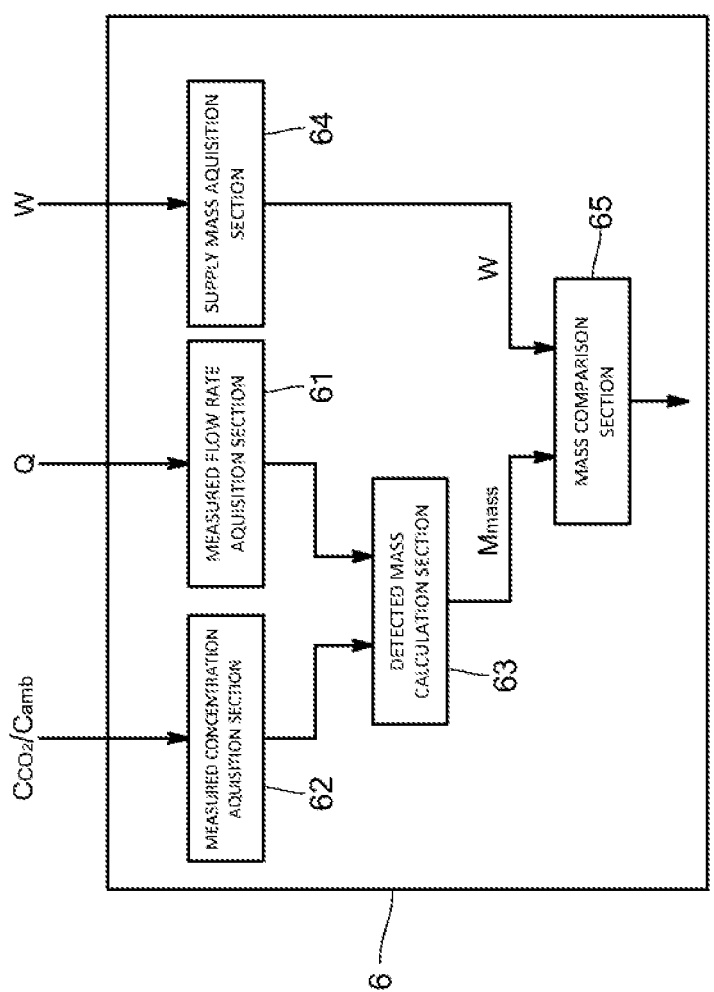
FIG. 3 is a schematic diagram that shows a functional configuration of an information processor in the present embodiment.

Upon execution of an inspection program being stored in the memory, the components of the information processor 6 cooperate with each other to cause the information processor 6 to function as at least a measured flow rate acquisition section 61, a measured concentration acquisition section 62, a detected mass calculation section 63 (background correction section), a supply mass acquisition section 64, and a mass comparison section 65 as shown in FIG. 3.

The measured flow rate acquisition section 61 is intended to acquire a measured flow rate obtained by the flowmeter 2, and acquires the measured flow rate from the flowmeter 2 over a period of time (measuring time) from the beginning of loading of $CO_2$ from the $CO_2$ gas cylinder 51 to the termination of the loading. Although the measured flow rate is acquired from the arithmetic unit 4 in the present embodiment, the measured flow rate may be acquired from the flowmeter 2. The measuring time is measured by the information processor 6.

The measured concentration acquisition section 62 is intended to acquire a $CO_2$ concentration obtained by the gas analyzer 3, and acquires the $CO_2$ concentration from the gas analyzer 3 over the measuring time. The measured concentration acquisition section 62 acquires a $CO_2$ concentration of background (hereinafter also referred to as a background concentration) obtained by the gas analyzer 3 in a state in which no standard gas is supplied to the flowmeter 2. Although the measured concentration or background concentration is obtained from the arithmetic unit 4 in the present embodiment, the measured concentration or background concentration may be acquired from the gas analyzer 3.

The detected mass calculation section 63 calculates a detected mass $M_{mass}$ g [g] of the in-vehicle exhaust gas analysis system 10 by using the measured flow rate G [L] obtained by the measured flow rate acquisition section 61, the $CO_2$ concentration $C_{CO2}$ [vol %] obtained by the measured concentration acquisition section 62, and the background concentration $C_{amb}$ [vol %] obtained by the measured concentration acquisition section 62. Specifically, the detected mass calculation section 63 integrates the detected mass $M_{mass}$ [g] in the measuring time from the following equation in which ρ is a gas density [g/L] of $CO_2$.

$$M_{mass} = \int (\rho \times Q \times (C_{co2} - C_{amb})) dt \quad \text{[Equation 2]}$$

The supply mass acquisition section 64 is intended to acquire a $CO_2$ mass (supply mass) supplied to the in-vehicle exhaust gas analysis system 10 by the standard gas supply mechanism 5. Specifically, the supply mass acquisition section 64 acquires a difference between a cylinder mass $W_1$ [g] of the $CO_2$ gas cylinder 51 before supplying $CO_2$ and a cylinder mass $W_2$ [g] after supplying $CO_2$ ($W=W_1-W_2$). The supply mass W [g] is obtainable by measuring a weight of the $CO_2$ gas cylinder 51 by an operator. Alternatively, the supply mass acquisition section 64 may calculate the supply mass W [g] by causing the supply mass acquisition section 64 to acquire data indicating the cylinder mass $W_1$ [g] before supplying $CO_2$ and the cylinder mass $W_2$ [g] after supplying $CO_2$.

The mass comparison section 65 is intended to calculate a relative error Err [%] of the detected mass $M_{mass}$ [g] relative to the supply mass W [g] by comparing the detected mass $M_{mass}$ [g] obtained by the detected mass calculation section 63, and the supply mass W [g] obtained by the supply mass acquisition section 64. Specifically, the mass comparison section 65 calculates the relative error Err [%] from the following equation.

$$Err = \left(\frac{M_{mass}}{W} - 1\right) \times 100 \quad \text{[Equation 3]}$$

Figure 4:
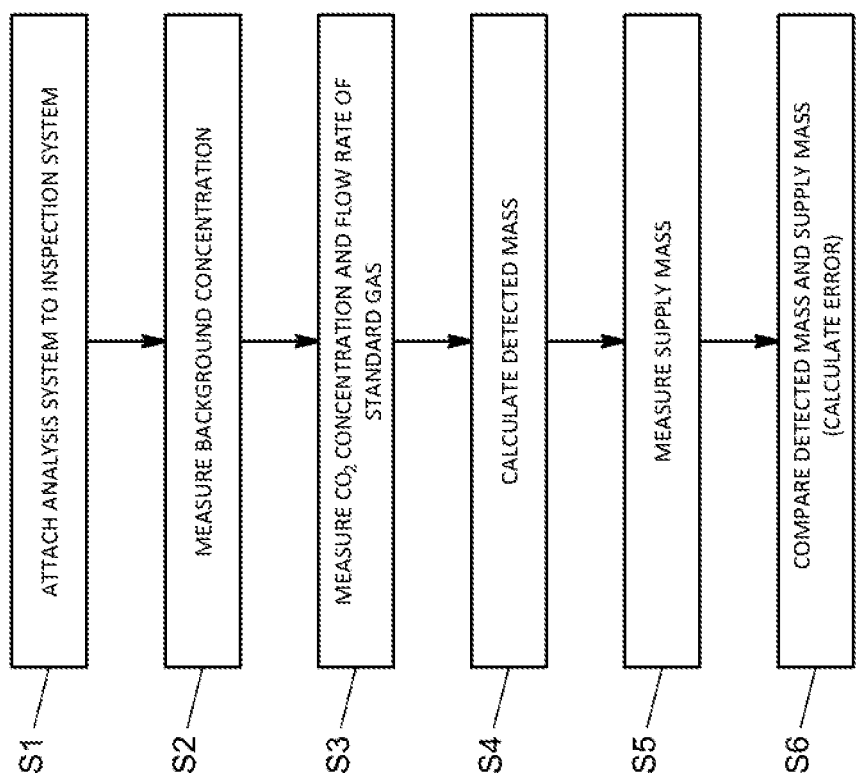
FIG. 4 is an inspection flowchart of the in-vehicle exhaust gas analysis system in the present embodiment.

An embodiment of an inspection procedure of the in-vehicle exhaust gas analysis system 10 is described below with reference to FIG. 4.

Firstly, the in-vehicle exhaust analysis system 10 is attached to the inspection system 100 (step S1). Specifically, the standard gas supply tube 52 and the standard gas discharge tube 531 are coupled to the mounting tube 21 of the flowmeter 2.

Subsequently, atmospheric air having a predetermined flow rate is supplied to the in-vehicle exhaust gas analysis system 10 by the flow rate regulating valve 532 and the suction pump 533 in the flow rate regulation section 53, without supplying $CO_2$ from the $CO_2$ gas cylinder 51. On this occasion, the gas analyzer 3 samples atmospheric air and measures a $CO_2$ concentration in the atmospheric air (a background concentration) (step S2). The background concentration is transmitted to the measured concentration acquisition section 62 of the information processor 6. The measurement of the background concentration may be carried out after the following measurement of a $CO_2$ concentration with the use of the standard gas (step S3).

Subsequently, $CO_2$ is supplied from the $CO_2$ gas cylinder 51, and standard gas having a predetermined flow rate is supplied to the in-vehicle exhaust gas analysis system 10 by the flow rate regulating valve 532 and the suction pump 533 in the flow rate regulation section 53. On this occasion, the flowmeter 2 measures a flow rate of the standard gas, and the gas analyzer 3 measures a $CO_2$ concentration of the standard gas (step S3). The flow rate of the standard gas is transmitted to the measured flow rate acquisition section 61, and the $CO_2$ concentration in the standard gas is transmitted to the measured concentration acquisition section 62.

The measuring time is approximately five minutes. During the measuring time, the flow rate may be made constant, or the flow rate may be changed stepwise or continuously within the flow rate range of the flowmeter 2.

Then, the detected mass calculation section 63 calculates a detected mass by using the obtained background concentration, the obtained flow rate of the standard gas, and the obtained $CO_2$ concentration of the standard gas (step S4).

The operator calculates a supply mass by measuring each of a mass of the $CO_2$ gas cylinder 51 before and after loading $CO_2$, and then inputs the supply mass to the information processor 6 with the use of input means (not shown) (step S5).

The mass comparison section 65 of the information processor 6 calculates a relative error by comparing the detected mass obtained by the detected mass calculation section 63 and the supply mass obtained by the supply mass acquisition section 64 (step S6). The calculated relative error is displayed on a display of the information processor 6. Alternatively, when the relative error is a predetermined threshold value or more (for example, ±2% or more), a determination may be made that this is a system error, and an error indication or the like may be performed.

Effects of Present Embodiment

With the inspection system 100 for the in-vehicle exhaust gas analysis system 10 according to the present embodiment so configured, the comparison is made between the detected mass calculated from the flow rate of the standard gas obtained by the flowmeter 2 and the concentration of the predetermined component obtained by the gas analyzer 3, and the supply mass of the predetermined component supplied to the in-vehicle exhaust gas analysis system 10. Therefore, the in-vehicle exhaust gas analysis system 10 is simply inspectable without the use of the CVS that has been used conventionally. Because there is no need to use the CVS, it is possible to eliminate the need for the preparation work for operating the chassis dynamometer and the work for carrying the in-vehicle exhaust gas analysis system 10 that has been mounted in the actual vehicle into the test room in which the CVS is disposed.

Other Embodiments

The present invention is not limited to the above embodiment.

For example, the flow rate is regulated by the flow rate regulating valve 532 and the suction pump 522 disposed on the standard gas discharge tube 531 in the present embodiment. Alternatively, the flow rate or $CO_2$ concentration of the standard gas supplied to the in-vehicle exhaust gas analysis system 10 may be regulated by disposing a supply-side flow rate regulation section, for example, by disposing a flow regulating value on the standard gas supply tube 52, or by disposing a flow rate regulating valve at the gas supply port 511 of the $CO_2$ gas cylinder 51.

By regulating the amount of supply of $CO_2$ from the $CO_2$ gas cylinder 51 with the use of a supply regulating part, such as a valve, and also by regulating the flow rate of the standard gas with the use of the flow rate regulation section 53, the flow rate and concentration of the standard gas supplied to the mounting tube 21 of the flowmeter 2 can be changed into a variety of combinations, such as a large flow rate and a low $CO_2$ concentration, a large flow rate and a high $CO_2$ concentration, a small flow rate and a high $CO_2$ concentration, and a small flow rate and a low $CO_2$ concentration.

When the in-vehicle exhaust gas analysis system 10 is inspected a plurality of times by the inspection system 100 of the above embodiment, the flow rates of the standard gas flown through in the inspections may differ from each other. In this case, it is also possible to focus on the inspection of the flowmeter 2 by being changed into a plurality of points within the measuring range of the flowmeter 2.

Although the $CO_2$ gas is used as the predetermined component of the standard gas in the inspection in the present embodiment, besides that, a predetermined component contained in the standard gas is selectable according to a detector of the gas analyzer 3.

In the above embodiment, the detected mass calculation section is intended to perform the background correction. Alternatively, a background correction section may be included separately, and the background correction section may subtract a background concentration from a concentration of a predetermined component obtained by the gas analyzer 3. In this case, the detected mass calculation section calculates a detected mass by using a predetermined component concentration corrected by the background correction section.

A mixing section, such as an orifice, may be disposed at the one end opening of the mounting tube 21 or in the vicinity thereof in order to make uniform the mixed gas of the standard gas supplied to the mounting tube 21 and atmospheric air.

Although the standard gas supply mechanism 5 in the present embodiment has the standard gas supply tube 52, the standard gas may be directly supplied from the gas supply port 511 of the standard gas source 51 to the one end opening of the mounting tube 21 instead of including the standard gas supply tube 52.

Moreover, the in-vehicle exhaust gas analysis system may be one which has the inspection function of the above embodiment. Specifically, the arithmetic unit 4 of the in-vehicle exhaust gas analysis system may be one which has, for example, the detected mass calculation section, the supply mass acquisition section, and the mass comparison section. Here, the in-vehicle exhaust gas analysis system may further include the standard gas supply mechanism of the above embodiment.

Furthermore, the information processor 6 is intended to calculate the detected mass by acquiring the measured flow rate and the measured concentration in the above embodiment. The information processor 6 may include the detected mass acquisition section to acquire a detected mass insofar as the detected mass is calculated by an external unit, for example, insofar as the arithmetic unit 4 of the in-vehicle exhaust gas analysis system 10 calculates the detected mass.

Although the exhaust gas analysis system of the above embodiment is configured to be mounted in the vehicle, the system may be a stationary one without being mounted on the vehicle, insofar as the configuration of each of the flowmeter and the exhaust gas analyzer remains identical or similar. Even in this case, the inspection is performable by applying a method similar to that in the above embodiment.

Although the exhaust gas analyzer is intended to measure the concentration of the measurement target component in the above embodiment, the exhaust gas analyzer may be configured to analyze the number of particles contained in exhaust gas or the mass of the particles. Even in this case, the inspection is performable by applying the method of the above embodiment.

Besides the above, it will be understood that the present invention is not limited to the above-described embodiment, and various modifications may be made without departing from the spirit and scope of the present invention.

DESCRIPTION OF THE REFERENCE NUMERAL

100 inspection system
V vehicle
EH exhaust pipe
10 in-vehicle exhaust gas analysis system
21 mounting tube
2 flowmeter
3 exhaust gas analyzer
5 standard gas supply mechanism
52 standard gas supply tube
53 flow rate regulation section
532 flow rate regulating valve
533 suction pump
63 detected mass calculation section
64 supply mass acquisition section
65 mass comparison section

What is claimed is:

1. An inspection system for inspecting an in-vehicle exhaust gas analysis system, the in-vehicle exhaust gas analysis system comprising a flowmeter, including a mounting tube to be externally attached to an exhaust pipe of a vehicle, to measure a flow rate of exhaust gas discharged from the vehicle, and an exhaust gas analyzer to analyze a concentration of a measurement target component contained in the exhaust gas, and the in-vehicle exhaust gas analysis system being configured to be supplied with a standard gas containing a predetermined component, the inspection system comprising:

a standard gas supply mechanism including a gas supply port configured to supply the standard gas to the flowmeter and the exhaust gas analyzer, and a gas supply tube configured to supply the standard gas to the mounting tube in a state in which the mounting tube is not attached to the exhaust pipe of the vehicle, wherein the standard gas supply mechanism is configured to permit an inflow of atmospheric air from around the gas supply port into the standard gas supply mechanism such that the standard gas and atmospheric air mix; and one or more processors programmed to
- calculate a detected mass of the predetermined component by using a flow rate obtained by the flowmeter and a concentration of the predetermined component obtained by the exhaust gas analyzer,
- acquire a supply mass of the predetermined component supplied to the flowmeter and the exhaust gas analyzer, and
- compare the detected mass and the supply mass, wherein the predetermined component is a component contained in the exhaust gas.

2. An in-vehicle exhaust gas analysis system comprising:
the inspection system for an in-vehicle exhaust gas analysis system according to claim 1; and
the flowmeter and the exhaust gas analyzer.

3. The in-vehicle exhaust gas analysis system according to claim 2, wherein the in-vehicle exhaust gas analysis system is configured to supply a mixed gas comprised of the standard gas and atmospheric air to the flowmeter and the exhaust gas analyzer, further comprising:
a flow rate control mechanism to control a flow rate of the mixed gas.

4. The in-vehicle exhaust gas analysis system according to claim 3, wherein the flow rate control mechanism is configured to stepwise or continuously change a flow rate of the mixed gas within a measuring range of the flowmeter.

5. The in-vehicle exhaust gas analysis system according to claim 2, wherein the standard gas supply mechanism further comprises a supply-side flow rate control section to control a flow rate of the standard gas supplied to the flowmeter and the exhaust gas analyzer.

6. The in-vehicle exhaust gas analysis system according to claim 2, wherein the one or more processors is further programmed to perform a background correction of the detected mass.

7. An inspection method for an in-vehicle exhaust gas analysis system that includes a flowmeter, including a mounting tube to be externally attached to an exhaust pipe of a vehicle, to measure a flow rate of exhaust gas discharged from the vehicle, and an exhaust gas analyzer to analyze a concentration of a measurement target component contained in the exhaust gas and to be supplied with a standard gas containing a predetermined component that is a component contained in the exhaust gas, the inspection method comprising:
supplying a standard gas to the flowmeter and the exhaust gas analyzer via a gas supply port of a standard gas mechanism such that atmospheric air from around the gas supply port is permitted to inflow with the standard gas;
supplying the standard gas to the mounting tube in a state in which the mounting tube is not attached to the exhaust pipe of the vehicle via a gas supply tube;
calculating a detected mass of the predetermined component supplied to the in-vehicle exhaust gas analysis system by using a flow rate obtained by the flowmeter and a concentration of the predetermined component obtained by the exhaust gas analyzer;
acquiring a supply mass of the predetermined component supplied to the in-vehicle exhaust gas analysis system; and
comparing the detected mass and the supply mass, wherein the predetermined component is a component contained in the exhaust gas.

8. An in-vehicle exhaust gas analysis system comprising:
a flowmeter, including a mounting tube to be externally attached to an exhaust pipe of a vehicle, configured to measure a flow rate of exhaust gas discharged from the vehicle;
an exhaust gas analyzer configured to analyze a concentration of a measurement target component contained in the exhaust gas, and to be supplied with a standard gas containing a predetermined component that is a component contained in the exhaust gas;
a standard gas supply mechanism including a gas supply port configured to supply the standard gas to the flowmeter and the exhaust gas analyzer, and a gas supply tube configured to supply the standard gas to the mounting tube in a state in which the mounting tube is not attached to the exhaust pipe of the vehicle, wherein the standard gas supply mechanism is configured to permit an inflow of atmospheric air from around the gas supply port; and
one or more processors programmed to
- calculate a detected mass of the predetermined component by using a flow rate obtained by the flowmeter and a concentration of the predetermined component obtained by the exhaust gas analyzer,
- acquire a supply mass of the predetermined component supplied to the flowmeter and the exhaust gas analyzer, and
- compare the detected mass and the supply mass.

9. The in-vehicle exhaust gas analysis system according to claim 8, wherein the in-vehicle exhaust gas analysis system is configured to supply a mixed gas comprised of the standard gas and atmospheric air to the flowmeter and the exhaust gas analyzer, further comprising:
a flow rate control mechanism to control a flow rate of the mixed gas.

10. The in-vehicle exhaust gas analysis system according to claim 9, wherein the flow rate control mechanism is configured to stepwise or continuously change a flow rate of the mixed gas within a measuring range of the flowmeter.

11. The in-vehicle exhaust gas analysis system according to claim 8, wherein the standard gas supply mechanism further comprises a supply-side flow rate control section to control a flow rate of the standard gas supplied to the flowmeter and the exhaust gas analyzer.

12. The in-vehicle exhaust gas analysis system according to claim 8, wherein the one or more processors is further programmed to perform a background correction of the detected mass.

* * * * *